United States Patent [19]

Barua et al.

[11] Patent Number: 5,061,723

[45] Date of Patent: Oct. 29, 1991

[54] NON-TERATOGENIC VITAMIN A PREPARATION FOR WOMEN OF CHILD-BEARING AGE

[75] Inventors: Arun B. Barua; Desiree Gunning; James A. Olson, all of Ames, Iowa

[73] Assignee: Iowa State University Research Foundation, Inc., Ames, Iowa

[21] Appl. No.: 355,779

[22] Filed: May 22, 1989

[51] Int. Cl.$^5$ .............................................. H61K 31/35
[52] U.S. Cl. .................... 514/460; 514/559; 514/725; 514/859
[58] Field of Search ............... 514/460, 559, 725, 859

[56] References Cited

U.S. PATENT DOCUMENTS 4,457,918  7/1984  Holick et al. ................... 424/180
4,855,463  8/1989  Barua et al. ................... 549/417

FOREIGN PATENT DOCUMENTS 1335887  10/1973  United Kingdom .

OTHER PUBLICATIONS

Gallup et al., *Proc. Soc. Exper. Biol. & Med.,* 186:269–274, (1987).
Zile et al., *Proc. Natl. Acad. Sci. U.S.A.,* vol. 84:2208–2212 (1987).
Rosa et al., *Teratology, 33:355–364 (1986).*
Gallup et al., First Mid–America Molecular Biol. Colloquium, p. 35, Oct. 1986.
Loeliger et al., Eur. J. Med. Chem., 15:9–15 (1980).
Pawson et al., J. Med. Chem., 25:1269–1277 (1982).
Kochhar et al., Toxic & Appl. Pharmacol., 96:429–441 (1988).
Bollag, Cancer Chemotherap. Pharmacol., 3:207–215 (1979).
Whillhite et al., Fd. Chem. Toxic, 23:51–55 (1985).
Eckhoff et al., Arch. Toxicol., 64:502–503 (1990).
Klug et al, Arch. Toxicol., 63:185–192 (1989).
Klug et al, Arch. Toxocol., 63:440–444 (1989).

*Primary Examiner*—Leonard Schenkman
*Attorney, Agent, or Firm*—Tilton, Fallon, Lungmus & Chestnut

[57] ABSTRACT

For treatment of acne the glucuronide of retinoic acid (retinoyl β-glucuronide) is orally administered to women of child-bearing age who are capable of conception. This therapy is safer than the oral administration of retinoic acid because retinoic acid glucuronide is essentially non-teratogenic at dose levels effective for the acne treatment. The retinoic acid glucuronide can be in all-trans or 13-cis form.

4 Claims, No Drawings

NON-TERATOGENIC VITAMIN A PREPARATION FOR WOMEN OF CHILD-BEARING AGE

GRANT REFERENCES

Research relating to the present invention was supported in part by grants from the U.S. Government; namely, USDA Grant 87-CRCR-1-2320 and NIH Grants DK32793 and 39733.

FIELD OF INVENTION

The field of this invention is the oral administration of retinoid compounds to women of child-bearing age. For oral treatment of acne in women who are capable of conception, retinoic acid (isotretinoin) has been administered with safeguards to avoiding pregnancy because of the known teratogenic properties of this compound. The present invention is concerned with the oral administration of a non-teratogenic form of retinoic acid to women of child-bearing age.

BACKGROUND OF INVENTION

Vitamin A (retinol) and most derivatives thereof having vitamin A activity are water-insoluble, being hydrophobic, lipid-soluble compounds. For example, retinoic acid is not water-soluble. It is known, however, that the glucuronide and glucose derivatives of retinoic acid and retinol are water-soluble. [See, for example, Lippel and Olson, *J. Lipid. Res.*, 9:580–586 (1968); Takabayashi, et al. *Chem. Abs.* 73:69834z (1970); Barua, et al., *Amer. J. Clin. Nutr.*, 43:481–485 (1986).] Water-soluble glycoside derivatives of vitamin A are described in U.S. Pat. No. 4,457,918. The retinoic acid glucuronide and retinol glucuronide have been tested for effects in vitro on cultures of HL-60 cells (a continuous human myeloid cell line): Gallup, et al., First Mid-America Molecular Biol. Colloquium, p. 35, October 1986, and *Proc. Soc. Exper. Biol. & Med.*, 186:269–274 (1987); and Zile, et al., *Proc. Nat. Acad. Sci. USA*, 84:2208–2212 (1987). Under the conditions of the HL-60 systems assay, activity similar to retinoic acid and retinol was reported. Both Gallup, et al. and Zile, et al. found that retinoyl $\beta$-glucuronide (retinoic acid glucuronide) was 50% less cytotoxic to HL-60 cells than all-trans retinoic acid.

The all-trans form of retinoic acid has been named tretinoin. Cream, gel, and liquid preparations containing tretinoin have been approved in the United States for treatment of acne. These preparations are being marketed under the trademark "Retin-A" by the Dermatological Division of Ortho Pharmaceutical Corporation, Raritan, N.J. The 13-cis form of retinoic acid has been named isotretinoin. Its use has been approved in the United States for oral treatment of severe acne (e.g., disfiguring cystic acne). Isotretinoin is marketed under the trademark "Accutane" by Roche Laboratories, Nutley, N.J., in 10, 20 and 40 milligram (mg) capsules. A typical dose range is from 0.5 to 2 mg/kg body weight per 24 hours. At these dose levels, isotretinoin is highly teratogenic.

When women of child-bearing age are being treated with isotretinoin for acne, extreme caution must be exercised to avoid the occurrence of a pregnancy during the treatment or at least one month after the treatment is discontinued. It is recommended that such woman patients not be treated with oral isotretinoin unless they agree to mandatory contraceptive measures and have had a negative serum pregnancy test prior to beginning the therapy. Major human fetal abnormalities relating to "Accutane" administration have been reported, and there is also an increased risk of spontaneous abortion. Other vitamin A congeners are also known to be teratogenic in animals and women. [See the teratogen update published by Rosa, et al., in *Teratology*, 33:355–364 (1986)].

SUMMARY OF INVENTION

This invention is based on the discovery that retinoic acid glucuronide (retinoyl $\beta$-glucuronide) is essentially non-teratogenic at normal dose levels for oral treatment of acne and other conditions requiring retinoid therapy for women of child-bearing age. This compound may be in an all-trans form or in a 13-cis form. It is believed that the 13-cis form is preferred. Since the retinoic compound of this invention is essentially non-teratogenic, high dose levels providing effective treatment for acne conditions, such as cystic acne or acne vulgaris, can be safely used. Where the acne is particularly resistant, it is believed feasible to use even higher doses than those which have heretofore been employed in women of child-bearing age without endangering the fetus if pregnancy should occur during treatment. It is also believed that other side effects which have been experienced with oral isotretinoin will be less evident.

DETAILED DESCRIPTION

Retinoic acid glucuronide (retinoyl $\beta$-glucuronide) is not commercially available but can be prepared by known synthesis procedures from commercially available starting materials. Retinoyl fluoride is a useful intermediate for preparing retinoic acid glucuronide. A method for preparing all-trans or 13-cis retinoyl fluoride is described in Barua and Olson, *Biochimica. et Biophysica Acta*, 757:288–299 (1983); and U.S. Pat. No. 4,473,503. A two-step process for preparing retinoic acid glucuronide from retinoyl fluoride is described in Barua and Olson, *J. Lipid. Res.*, 26:1277–1282 (1985). Retinoyl fluoride is first reacted with 6,3-glucuronolactone to produce 6,3-lactone of retinoyl glucuronic acid, which is then hydrolyzed with dilute alkali to give the retinoyl $\beta$-glucuronide. A one-step process for this synthesis is described in U.S. patent application Ser. No. 941,637, filed Dec. 15, 1986. The reaction is carried out in an acetone-water mixture proportioned so that both the water-insoluble retinoyl fluoride and the water-soluble glucuronic acid are maintained in solution.

This invention is concerned with the treatment of women of child-bearing age for acne or other condition requiring oral retinoid therapy. Although the women are capable of conception, the compound of this invention can be administered in effective amounts without the danger of teratogenicity if the woman patient becomes pregnant during the therapy or shortly thereafter. It is believed that if necessary retinoic acid glucuronide can even be orally administered to pregnant women without teratogenic consequences.

Oral doses of retinoic acid glucuronide can range from 0.25 to 4 milligrams (mg) per kilogram of the patient's body weight per 24 hours. This refers to total doses, which may be divided into two or more individual doses within each 24 hour period. For most purposes, such as the treatment of cystic acne, it is believed that the preferred dose range will be from about 0.5 to 2 mg/kg body weight/24 hrs. The retinoic acid glucuronide should be prepared in premeasured oral dose units. For example, the dose units may comprise tablets or capsules, and each tablet or each capsule should contain an amount of the compound for convenient administration, such as 10, 20, or 40 mg. Incorporation of the compound in the form of a dry powder in gelatin capsules provides a convenient dose unit. Alternatively, the compound in the form of a dry powder may be tabletted, and for this purpose may be combined with a tabletting sugar or other diluent such as lactose.

The method of this invention is further illustrated by the following examples.

EXAMPLE I

Synthesis of Retinoyl β-Glucuronide

Retinoic Acid Glucuronide

Retinoyl fluoride (2.4 g, 7.9 mmol) was dissolved in 200 ml of acetone. D-glucuronic acid (6 g, 31 mmol) dissolved in 50 ml of water and sodium bicarbonate (970 mg) dissolved in 50 ml of water were added to the retinoyl fluoride solution. The mixture was stirred at room temperature for 20–24 hrs. The solution was neutralized with 1N HCl, diluted with water, and the product was extracted with ethyl acetate. The extract was washed with water, dried over anhydrous sodium sulfate and then evaporated to dryness in a rotary evaporator. The residue was dissolved in 2–3 ml of diethyl ether and transferred to a silica gel (for dry column chromatography, wet packed with hexane) column. The column was developed with hexane containing diethyl ether (5–50%) to remove retinoic acid and other products. The major yellow band containing retinoyl glucuronide was next eluted with a mixture of $CH_2Cl_2/CH_3OH$ (1:1). The solvent was evaporated to dryness to give solid retinoyl β-glucuronide (2.3 g, 60%). This preparation consisted mainly of the all-trans isomer, and can be used as such.

An analytically pure sample of retinoyl β-glucuronide was obtained by HPLC of the above preparation on a Whatman ODS-3 column (M9, 50 cm) using methanol/water (7:3) containing 10 mM ammonium acetate at a flow rate of 3 ml/min. Retinoyl β-glucuronide ($t_R = 49.7$ min) separated from traces of isomers or anomers ($t_R = 46.4$ min). The eluate carrying retinoyl β-glucuronide was diluted with water and made just acidic with 0.1N HCl. The product was extracted with ethyl acetate. The extract was washed with water, dried over anhydrous sodium sulfate, and then evaporated to dryness. The residue was dissolved in a small volume of diethyl ether and all-trans retinoyl β-glucuronide was precipitated with hexane. The solid was separated and dried. All-trans retinoyl β-glucuronide:m.p. 142°–143° C. (darkens at 125° C.); $UV_{max}360$ nm ($E_{1cm}=1065$) in methanol and 365 nm in water. The $^1$H-NMR, IR and Mass spectra and C, H analysis results were consistent with the structure. The compound is soluble in water. Incubation of retinoyl β-glucuronidase (from *E. coli*) in phosphate buffer (pH 6.8) for 0.5–2 hrs generated retinoic acid.

EXAMPLE II

All-trans retinoic acid glucuronide was tested for teratogenicity in pregnant rats.

Experimental Plan

The retinoic acid glucuronide dissolved in vegetable oil. Equivalent amount of all-trans retinoic acid was also dissolved in the vegetable oil. Groups of pregnant rats were dosed orally with either retinoid glucuronide or retinoic acid on day 8.5 of gestation. This particular day was chosen because other workers have demonstrated that maximal fetal damage results when teratogens are administered on day 8–10 of gestation in the rat. The rats were killed on day 19.5 of a 21 day gestational period, and the fetuses were examined for viability, growth, and developmental abnormalities.

Experimental Procedure

Rats that became pregnant during the same night were selected for the study. The rats were divided into 3 groups. Rats in Group 1 received orally 55 mg of the all-trans retinoic acid glucuronide (equivalent to 35 mg of retinoic acid) or a very large dose of 108 mg of the glucuronide in peanut oil. Rats in Group 2 received orally 35 mg of all-trans retinoic acid in peanut oil. Rats in Group 3 received no retinoid and served as control. The rats were then allowed to grow normally and on day 19, they were killed and fetuses were examined.

Results

It was observed that the rats given large doses of the retinoid glucuronide did not show any sign of teratogenicity. All the pups were normal and live. On the other hand, the rats given the same large doses of retinoic acid did not carry the pregnancy to term—all the embryos died and were being resorbed. Results are summarized in Table A.

TABLE A

| Dams (No.) | Compound Tested | Dose/ Rat (mg) | Live Birth (%) | Resorbed[1] (%) |
|---|---|---|---|---|
| 3 | Retinoyl glucuronide | 55 | 100 | 0.03 |
| 1 | Retinoyl glucuronide | 108 | 100 | 0 |
| 3 | Retinoic acid | 35 | 0 | 100 |
| 5 | None (control) | 0 | 100 | 0.04 |

[1]At implantation of fetus.

We claim:

1. A method of treating acne in a woman patient of child-bearing age who is capable of conception, comprising orally administering to said patient retinoic acid glucuronide, said glucuronide being in an all-trans or 13-cis form and being administered in an effective amount for said acne treatment.

2. The method of treating acne of claim 1 in which said glucuronide is in an all-trans form.

3. The method of treating acne of claim 1 in which said glucuronide is in a 13-cis form.

4. The method of treating acne of claims 1, 2 or 3 in which the amount of said glucuronide administered to said patient is from about 0.5 to 2 milligrams per kilogram of patient body weight per 24 hours.

* * * * *